United States Patent [19]
Wallquist et al.

[11] Patent Number: 5,817,832
[45] Date of Patent: Oct. 6, 1998

[54] BLUE DIKETOPYRROLOPYRROLE PIGMENTS

[75] Inventors: Olof Wallquist; Bernd Lamatsch; Thomas Ruch, all of Marly, Switzerland

[73] Assignee: Ciba Specialty Chemicals Corporation, Tarrytown, N.Y.

[21] Appl. No.: 664,271

[22] Filed: Jun. 11, 1996

[30] Foreign Application Priority Data

Jun. 22, 1995 [CH] Switzerland .................. 1836/95

[51] Int. Cl.⁶ .................................................. C07D 487/04
[52] U.S. Cl. .................................... 548/453; 544/144
[58] Field of Search .................................... 548/453

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,659,775 | 4/1987 | Pfenninger et al. | 524/92 |
| 4,720,305 | 1/1988 | Iqbal et al. | 106/288 |
| 4,783,540 | 11/1988 | Bäbler | 548/453 |
| 4,810,802 | 3/1989 | Wallquist et al. | 548/453 |
| 5,200,528 | 4/1993 | Wooden et al. | 548/453 |

FOREIGN PATENT DOCUMENTS

| | | |
|---|---|---|
| 0353184 | 1/1990 | European Pat. Off. |
| 0511165 | 10/1992 | European Pat. Off. |

OTHER PUBLICATIONS

Chemical Abstract 113: 68369j of JP0255,362 (1990).
12th Collective Index, p. 81755, Cl (42,86–89), p. 81756, cl (5–8, 25–32) c2 (64–67), (1990).

*Primary Examiner*—Robert W. Ramsuer
*Attorney, Agent, or Firm*—Kevin T. Mansfield; Michele A. Kovaleski

[57] ABSTRACT

Diketopyrrolo[3,4-c]pyrroles of the formula

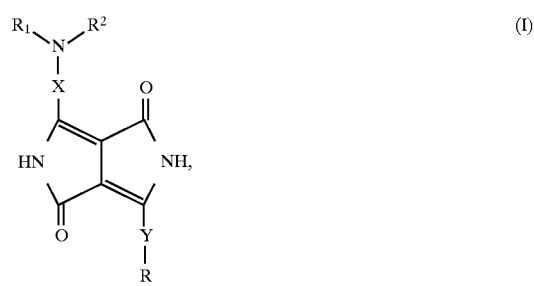

in which X and Y independently of one another are a divalent aromatic radical and R is a radical CN, $COR_5$, $CO_2R_5$, $CON(R_5)_2$, $NO_2$, $SO_2R_5$, $SOR_5$, $SO_2N(R_5)_2$ or $PO(OR_6)_2$.

For the definition of the substituents $R_1$, $R_2$ and $R_5$, refer to claim 1.

These compounds are blue to violet, tinctorially strong pigments with good stability properties, in particular good light stability and weather stability.

5 Claims, No Drawings

BLUE DIKETOPYRROLOPYRROLE PIGMENTS

The present invention relates to novel, stable, blue to violet diketopyrrolopyrroles and to their use as pigments.

1,4-Diketopyrrolo[3,4-c]pyrroles have been known for some years as pigments having excellent pigment properties, for example from U.S. Pat. No. 4,415,685, where diketopyrrolopyrroles of the formula

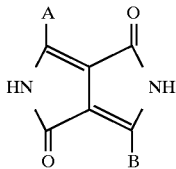

in which A and B are isocyclic or heterocyclic radicals, preferably mono- to tetracyclic radicals, especially mono- or bicyclic radicals, are described as being red pigments with a very clean colour, high tinctorial strength and good stability properties, for example light stability, weather stability, heat resistance and migration resistance. The ready suitability of such products as pigments with an orange to, in particular, red shade is also confirmed in numerous subsequent patents, as for example in U.S. Pat. No. 4,579,949, U.S. Pat. No. 4,720,305, U.S. Pat. No. 4,810,802, U.S. Pat. No. 4,783,540, U.S. Pat. No. 5,200,528, etc. In U.S. Pat. No. 4,579,949, a description is also given of a diketopyrrolopyrrole of the abovementioned formula in which A and B are p-dimethylaminophenyl as a blue pigment. However, this pigment does not meet the current requirements of the industry with respect to its stability to light and weather.

It has now been found that diketopyrrolopyrroles of the abovementioned formula in which A and B are two different, substituted aromatic radicals of which one contains an amino group are, quite surprisingly, blue to violet pigments having improved pigment properties, especially light stability and weather stability.

The present invention accordingly provides diketopyrrolo[3,4-c]pyrroles of the formula

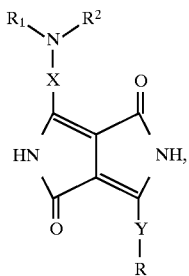 (I)

in which X and Y independently of one another are a divalent aromatic radical of the formula

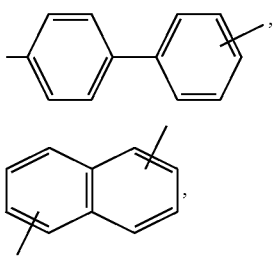

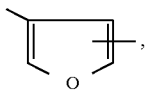

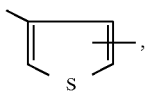

or, in particular,

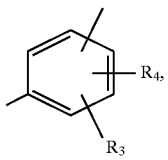

R is a radical CN, $COR_5$, $CO_2R_5$, $CON(R_5)_2$, $NO_2$, $SO_2R_5$, $SOR_5$, $SO_2N(R_5)_2$ or $PO(OR_6)_2$, $R_3$ and $R_4$ independently of one another are hydrogen, chlorine, bromine, methyl, ethyl, methoxy or ethoxy, $R_6$ is $C_1$–$C_6$alkyl or phenyl, $R_1$, $R_2$ and $R_5$ independently of one another are hydrogen, $C_1$–$C_{18}$alkyl, $C_1$–$C_{18}$alkenyl, or phenyl which is unsubstituted or substituted by chlorine, bromine, hydroxyl, $C_1$–$C_6$alkyl, $C_1$–$C_6$alkoxy, $C_1$–$C_6$alkylmercapto, CN, $NO_2$ or $CF_3$, or $R_1$ and $R_2$, together with the nitrogen atom to which they are attached, form a 5- or 6-membered heterocyclic radical which is unsubstituted or substituted by $C_1$–$C_6$alkyl or phenyl and is selected from the group consisting of pyrrolidinyl, piperidyl, pyrrolyl, triazolyl, imidazolyl, pyrazolyl, piperazinyl, morpholinyl, thiomorpholinyl, carbazol-1-yl, indol-1-yl, indazol-1-yl, benzimidazol-1-yl, tetrahydroquinol-1-yl and tetrahydroquinol-2-yl, or, if $R_1$ is hydrogen, $R_2$ is a radical of the formula

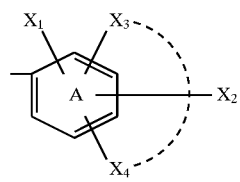

in which $X_1$ and $X_2$ independently of one another are hydrogen, chlorine, bromine, $NO_2$, methyl, methoxy or ethoxy and $X_3$ and $X_4$ form a 5- or 6-membered heterocyclic ring which together with A produces a benzimidazolonyl, dihydroxyquinazolinyl, quinolonyl, benzoxazolonyl, phenmorpholonyl, quinazolinonyl or phthalimidyl radical or a radical of the formula

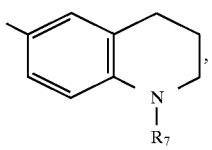

in which $R_7$ is $C_1$–$C_6$alkyl or phenyl, or Y-R can be a radical

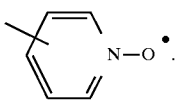

$C_1$–$C_6$Alkyl is for example methyl, ethyl, n-propyl, isopropyl, n-butyl, sec-butyl, tert-butyl, amyl or hexyl and $C_1$–$C_{18}$alkyl is additionally for example heptyl, octyl, 2-ethylhexyl, nonyl, decyl, dodecyl, tetradecyl, hexadecyl or octadecyl. $C_1$–$C_6$Alkyl can also have the same meaning in $C_1$–$C_6$alkylmercapto.

$C_2$–$C_{18}$Alkenyl is for example vinyl, allyl, methallyl, n-but-2-enyl, 2-methylprop-2-enyl, n-pent-2-enyl, n-hex-2-enyl, n-oct-2-enyl, n-dec-2-enyl, n-dodec-2-enyl or octadec-5-enyl.

$C_1$–$C_6$Alkoxy is for example methoxy, ethoxy, n-propoxy, isopropoxy, n-butoxy, tert-butoxy, n-pentoxy, tert-amyloxy or hexyloxy.

The long valency bond in the case of $X_2$ indicates that $X_2$ can be either in the aromatic ring A or in the heterocycle.

The radicals of the formula

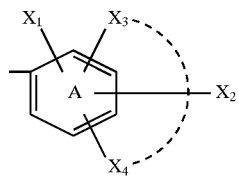

for $R_2$ are derived from amines of the formula

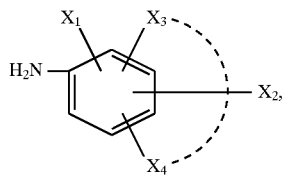

in which $X_1$–$X_4$ are as defined above.

Examples hereof are: 5-aminobenzimidazolone, 7-chloro-5-aminobenzimidazolone, 7-bromo-5-aminobenzimidazolone, 6-chloro-5-aminobenzimidazolone, 6-bromo-5-amino-benzimidazolone, 6-methoxy-5-aminobenzimidazolone, 7-methoxy-5-aminobenzimidazolone, 6-ethoxy-5-aminobenzimidazolone, 7-chloro-4-methyl-5-aminobenzimidazolone, 6-methyl-5-aminobenzimidazolone, 4,7 dimethyl-5-aminobenzimidazolone, 4-methyl-6-chloro-5-aminobenzimidazolone, 5-amino-1-methylbenzimidazolone, 6-amino-2,4-dihydroxyquinazoline, 6-amino-1,4-dihydroxyquinazoline, 6-amino-4-methyl-2-quinolone, 7-amino-4-methyl-2-quinolone, 7-amino-4,6-dimethyl-2-quinolone, 6-amino-7-chloro-4-methyl-2-quinolone, 7-amino-4-methyl-6-methoxy-2-quinolone, 5-aminobenzoxazolone, 6-aminobenzoxazolone, 6-amino-5-methylbenzoxazolone, 6-amino-5-chlorobenzoxazolone, 6-amino-3-phenmorpholone, 7-amino-3-phenmorpholone, 7-amino-6-chloro-3-phenmorpholone, 7-amino-6-methyl-3-phenmorpholone, 7-amino-6-methoxy-3-phenmorpholone, 6-amino-4-methyl-3-phenmorpholone, 7-amino-4-methyl-3-phenmorpholone, 7-amino-4,6-dimethyl-3-phenmorpholone, 6-amino-4-quinazolinone and 5-aminophthalimide.

Diketopyrrolo[3,4-c]pyrroles of the formula I which are of particular interest are those in which X and Y independently of one another are

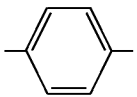

or

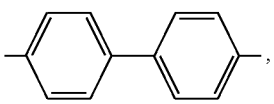

R is a radical CN, $NO_2$, $CO_2R_5$ or $CON(R_5)_2$, $R_1$, $R_2$ and $R_5$ independently of one another are hydrogen, $C_1$–$C_6$alkyl, or phenyl which is unsubstituted or substituted by chlorine, bromine, $C_1$–$C_5$alkyl, methoxy, CN or $NO_2$, or $R_1$ and $R_2$, together with the nitrogen atom to which they are attached, form pyrrolidinyl or piperidine.

Preference is given to diketopyrrolo[3,4-c]pyrroles of the formula I in which X and Y are

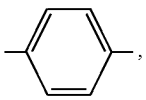

R is a radical CN or $NO_2$, $R_1$ and $R_2$ independently of one another are hydrogen, methyl, or phenyl which is unsubstituted or substituted by methyl, methoxy, ethoxy, Cl or $NO_2$, or $R_1$ and $R_2$, together with the nitrogen atom to which they are attached, form pyrrolidinyl or piperidyl. $R_1$ and $R_2$ are preferably identical.

The novel diketopyrrolo[3,4-c]pyrroles of the formula I can be prepared in analogy to generally known processes, for example by reacting a diketopyrrolo[3,4-c]pyrrole of the formula

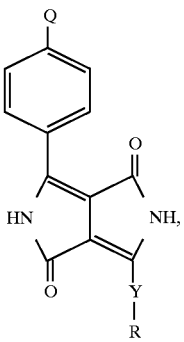

(II)

in which Q is bromine or, preferably, fluorine, and especially chlorine, and Y and R are as defined above, with an amine of the formula

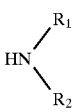

(III)

as is described, for example, in EP-A 353 184.

The diketopyrrolo[3,4-c]pyrroles of the formula II are known substances. Should some of them be novel, they can be prepared in analogy to generally known processes, for example by reacting a pyrrolinone of the formula

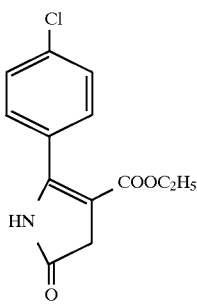

with a nitrile of the formula R—Y—CN (V) as described, for example, in U.S. Pat. No. 4,659,775.

The compounds of the formulae III, IV and V are known substances. Should some of them be novel, they can be prepared by generally known processes.

The novel diketopyrrolo[3,4-c]pyrroles can be used as pigments for colouring high molecular weight organic material.

High molecular weight organic materials which can be pigmented with the novel diketopyrrolo[3,4-c]pyrroles are, for example, cellulose ethers and cellulose esters, such as ethylcellulose, nitrocellulose, cellulose acetate, cellulose butyrate, natural resins or synthetic resins, such as resins formed by addition polymerization or by condensation, such as amino resins, especially urea- and melamine-formaldehyde resins, alkyd resins, phenolic resins, polycarbonates, polyolefins, polystyrene, polyvinyl chloride, polytetrafluoroethylene, polyamides, polyurethanes, polyesters, polyether ketones, polyphenylene oxides, rubber, casein, silicone and silicone resins, individually or in mixtures.

The abovementioned high molecular weight organic compounds can be present individually or in mixtures as plastic masses, as melts or in the form of spinning solutions, varnishes, paints or printing inks. Depending on the intended use it may be advantageous to employ the novel diketopyrrolo[3,4-c]pyrroles as toners or in the form of preparations. Based on the high molecular weight organic material to be pigmented, the novel diketopyrrolo[3,4-c] pyrroles can be employed in a quantity of from 0.01 to 30% by weight, preferably from 0.1 to 10% by weight.

For pigmenting paints and printing inks, the high molecular weight organic materials and the novel diketopyrrolo[3,4-c]pyrroles, together if desired with additives, such as fillers, other pigments, siccatives or plasticisers, are finely dispersed or dissolved in a mutual organic solvent or solvent mixture. In this context it is possible to follow a procedure in which the individual components are dispersed or dissolved individually, or else a number are dispersed or dissolved together, and only after this are all of the components combined.

The resulting blue to violet colorations, for example in plastics, fibres, paints or prints, are distinguished by good general properties, such as high tinctorial strength, good dispersibility, good fastness to overcoating and migration, good heat resistance and, in particular, by good light stability and weather stability.

The examples which follow illustrate the invention.

EXAMPLE 1

In an autoclave, 5.0 g of 3-(4-chlorophenyl)-6-(4-cyanophenyl)-2,5-dihydropyrrolo[3,4-c]pyrrole-1,4-dione (previously referred to in the patent literature as 1,4-diketo-3-(4-chlorophenyl)-6-(4-cyanophenyl)pyrrolo[3,4-c]pyrrole) are suspended in 100 ml of N-methylpyrrolidone. 10.7 g of dimethylamine gas are then fed in and the mixture is stirred at 180° C. for 10 hours. The mixture is subsequently rinsed out with N-methylpyrrolidone and filtered, and the solid product is washed with methanol and water until colourless and dried at 80° C. in a vacuum oven, to give 3.6 g of a blue-violet powder.

| Analysis ($C_{21}H_{16}N_4O_2$): | C | H | N |
|---|---|---|---|
| calc.: | 70.8% | 4.5% | 15.7% |
| found: | 69.8% | 4.5% | 15.4% |

EXAMPLE 2

Following the procedure of Example 1, 3.8 g of 3-(4-chlorophenyl)-6-(4-cyanophenyl)-2,5-dihydropyrrolo[3,4-c]pyrrole-1,4-dione are reacted with 13.8 g of pyrrolidine in 80 ml of N-methylpyrrolidone, giving 0.45 g of a blue-violet powder.

| Analysis ($C_{23}H_{18}N_4O_2$): | C | H | N |
|---|---|---|---|
| calc.: | 72.2% | 4.7% | 14.6% |
| found: | 70.9% | 4.7% | 14.5% |

EXAMPLE 3

Following the procedure of Example 1, 10.0 g of 3-(4-chlorophenyl)-6-(4-dimethylaminocarbonylphenyl)-2,5-dihydropyrrolo[3,4-c]pyrrole-1,4-dione are reacted with 18.7 g of dimethylamine in 200 ml of N-methylpyrrolidone, giving 0.3 g of a blue-violet powder in which the chlorine in the starting material has been substituted for dimethylamino to the extent of about 44% (Cl analysis).

| Analysis ($C_{23}H_{28}N_4O_3$): | C | H | N | Cl |
|---|---|---|---|---|
| calc.: | 68.6% | 5.5% | 13.9% | 0% |
| found: | 60.2% | 3.9% | 9.0% | 5.0% |

EXAMPLE 4

1.0 g of the product obtained in Example 1 is dissolved at 0° C. in 10 ml of concentrated sulfuric acid and the solution is stirred under nitrogen for 16 hours, allowing the reaction mixture to come slowly back to room temperature. The reaction mixture is subsequently poured into an ice-water mixture and neutralized with 30% sodium hydroxide solution. The pigment is filtered off on a suction filter, rinsed with 100 ml of water and dried overnight in an oven, giving 0.95 g of a blue-violet powder.

| Analysis ($C_{21}H_{18}N_4O_3$): | C | H | N |
|---|---|---|---|
| calc.: | 67.4% | 4.9% | 15.0% |
| found: | 65.8% | 5.2% | 14.6% | no longer any CN signal in the IR.

EXAMPLE 5

A solution of 32.4 g of 3-(4-chlorophenyl)-6-phenyl-2,5-dihydropyrrolo[3,4-c]pyrrole-1,4-dione in 740 g of anhydrous sulfuric acid is cooled to 0° C., and 10.6 g of potassium nitrate are added at this temperature over the course of one hour. After stirring for a further five hours during which the temperature does not exceed +5° C., the resulting solution is discharged, while continually stirring with a toothed disc, onto 2000 parts of ice. Filtering of the resulting suspension, washing of the solid product to neutrality with water and drying thereof at 80° C. in vacuo give 19.4 g of a violet pigment.

| Analysis ($C_{18}H_{10}ClN_3O_4$): | C | H | N | Cl |
|---|---|---|---|---|
| calc.: | 58.8% | 2.7% | 11.4% | 9.6% |
| found: | 58.0% | 2.9% | 11.0% | 9.6% |

EXAMPLE 6

3.67 g of the pigment obtained in Example 5 are suspended in 100 parts of N-methylpyrrolidone, and 10 g of dimethylamine are injected in an autoclave. After heating at 180° C. with stirring for 10 hours, the suspension obtained is cooled to room temperature and is discharged, while continually stirring with a toothed disc, into 1000 g of water. After thorough washing with water and drying at 80° C. in vacuum, 1.6 g of a violet pigment are obtained.

| Analysis ($C_{20}H_{16}N_4O_4$): | C | H | N | Cl |
|---|---|---|---|---|
| calc.: | 63.8% | 4.3% | 14.9% | 0.0% |
| found: | 66.8% | 5.2% | 14.4% | 2.2% |

EXAMPLE 7

Following the procedure of Example 1, 4.3 g of 3-(4-chlorophenyl)-6-(6-cyanonaphth-2-yl)-2,5-dihydropyrrolo[3,4-c]pyrrole-1,4-dione are reacted with 9.0 g of dimethylamine in 100 ml of N-methylpyrrolidone, giving 3.7 g of a blue-violet powder.

| Analysis ($C_{25}H_{18}N_4O_2$): | C | H | N | Cl |
|---|---|---|---|---|
| calc.: | 73.9% | 4.5% | 13.8% | 0% |
| found: | 72.6% | 4.3% | 13.0% | 1.9% |

EXAMPLE 8

Following the procedure of Example 1, 5.2 g of 3-(4-chlorophenyl)-6-(4-cyanobiphenyl)-2,5-dihydropyrrolo(3,4-c)pyrrole-1,4-dione are reacted with 10.9 g of dimethylamine in 100 ml of N-methylpyrrolidine, giving 2.8 g of a blue-violet powder.

| Analysis ($C_{27}H_{20}N_4O_2$): | C | H | N | Cl |
|---|---|---|---|---|
| calc.: | 74.99% | 4.66% | 12.95% | 0% |
| found: | 73.9% | 4.6% | 12.6% | 0.9% |

EXAMPLE 9

7.5 g of the pigment from Example 1, 98.9 g of CAB solution consisting of 41.0 g of cellulose acetobutyrate ®CAB 531.1, 20% in butanol/xylene 2:1 (Eastman Chem.)

1.5 g of zirconium octoate, 18.5 g of ®SOLVESSO 150* (ESSO), 21.5 g of butyl acetate and 17.5 g of xylene, 36.5 g of polyester resin ®DYNAPOL H700 (Dynamit Nobel), 4.6 g of melamine resin MAPRENAL MF650 (Hoechst) and 2.5 g of dispersant ®DISPERBYK 160 (Byk Chemie) are dispersed together on a shaker machine for 90 minutes (total coating material 150 g; 5% pigment).

*Aromatic hydrocarbons 27.69 g of the resulting masstone coating material are mixed, for the basecoat finish, with 17.31 g of Al stock solution (8% strength) consisting of 12.65 g of ®SILBERLINE SS 3334AR, 60% (Silberline Ltd.)

56.33 g of CAB solution (composition as above)

20.81 g of polyester resin ®DYNAPOL H700

2.60 g of melamine resin ®MAPRENAL MF650

7.59 g of ®SOLVESSO 150 and are applied by spraying to an aluminium panel (wet film about 20 μm). After a flash-off time of 30 minutes at room temperature, a thermosetting acrylic varnish consisting of 29.60 g of acrylic resin ®URACRON 2263 XB, 50% in xylene/butanol (Chem. Fabrik Schweizerhalle), 5.80 g of melamine resin ®CYMEL 327, 90% in isobutanol, 2.75 g of butylglycol acetate, 5.70 g of xylene, 1.65 g of n-butanol 0.50 g of silicone oil, 1% in xylene, 3.00 g of light stabilizer ®TINUVIN 900, 10% in xylene (Ciba)

1.00 g of light stabilizer ®TINUVIN 292, 10% in xylene (Ciba)

is applied by spraying as a topcoat finish (wet film about 50 μm). After a further flash-off time of 30 minutes at room temperature, the coating material is subsequently baked at 130° C. for 30 minutes, to give a blue-violet coating with very good stability properties.

EXAMPLE 10

0.6 g of the pigment of Example 1 is mixed with 67 g of polyvinyl chloride, 33 g of dioctyl phthalate, 2 g of dibutyltin dilaurate and 2 g of titanium dioxide and the mixture is processed on a roller gear bed at 160° C. for 15 minutes to form a thin film. The blue-violet PVC film thus produced shows high colour strength and is resistant to migration and stable to light.

EXAMPLE 11

1000 g of polypropylene granules (®DAPLEN PT-55, Chemie LINZ) and 20 g of a 50% strength pigment preparation, consisting of 10 g of the pigment of Example 1 and 10 g of magnesium behenate, are mixed intensively in a mixing drum. The granules thus treated are spun at from 260° to 285° C. by the melt spinning process, giving fibres coloured in a blue-violet shade with very good light fastness and textile fastness properties.

What is claimed is:

1. A diketopyrrolo[3,4-c]pyrrole of the formula

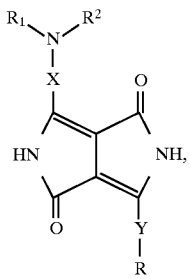 (I)

in which

X is unsubstituted phenylene,

Y is unsubstituted phenylene or a divalent aromatc radical of the formula

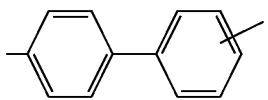

or

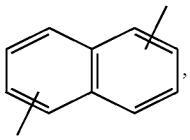

R is a radical CN, $NO_2$, or $CON(R_5)_2$ in which $R_5$ is hydrogen or $C_1$–$C_6$alkyl, and $R_1$ and $R_2$, independently of one another are hydrogen, $C_1$–$C_{18}$alkyl, $C_1$–$C_{18}$alkenyl, or phenyl which is unsubstituted or substftuted by chlorine, bromine, hydroxyl, $C_1$–$C_8$alkyl, $C_1$–$C_8$alkoxy, $C_1$–$C_8$alkylmercapto, CN, $NO_2$ or $CF_3$, or $R_1$ and $R_2$, together with the nitrogen atom to which they are attached, form a pyrrolidinyl or piperidinyl radical.

2. A diketopyrrolo[3,4-c]pyrrole according to claim 1 of the formula I in which X and Y are unsubstituted phenylene, R is a radical CN, $NO_2$, or $CON(R_5)_2$ in which $R_5$ is hydrogen or methyl, and $R_1$ and $R_2$, independently of one another are hydrogen, $C_1$–$C_6$alkyl, or phenyl which is unsubstituted or substituted by chlorine, bromine, $C_1$–$C_5$ alkyl or methoxy.

3. A diketopyrrolo[3,4-c]pyrrole according to claim 1 of the formula I in which X is unsubstituted phenylene, Y is unsubstituted phenylene or a divalent aromatic radical of the formula

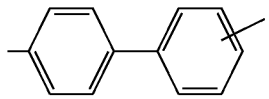

or

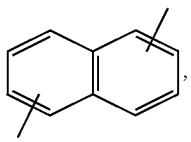

R is a radical CN and $R_1$ and $R_2$ independently of one another are hydrogen, $C_1$–$C_{18}$alkyl, $C_1$–$C_{18}$alkenyl, or phenyl which is unsubstituted or substituted by chlorine, bromine, hydroxyl, $C_1$–$C_6$alkyl, $C_1$–$C_6$alkoxy, $C_1$–$C_6$alkylmercapto, CN, $NO_2$ or $CF_3$.

4. A diketopyrrolo[3,4-c]pyrrole according to claim 1 of the formula I in which X and Y are

R is a radical CN or $NO_2$, $R_1$ and $R_2$ independently of one another are hydrogen, methyl, or phenyl which is unsubstituted or substituted by methyl, methoxy, ethoxy, Cl or $NO_2$, or $R_1$ and $R_2$, together with the nitrogen atom to which they are attached, form pyrrolidinyl or piperidyl.

5. A diketopyrrolo[3,4-c]pyrrole according to claim 4 of the formula I in which $R_1$ and $R_2$ are identical.

* * * * *